(12) United States Patent
Gasanz Guillén et al.

(10) Patent No.: US 8,188,285 B2
(45) Date of Patent: May 29, 2012

(54) PURIFICATION PROCESS OF MONTELUKAST AND ITS AMINE SALTS

(75) Inventors: Yolanda Gasanz Guillén, Barcelona (ES); Pedro Talavera Escasany, Barcelona (ES); Montserrat Monsalvatje Llagostera, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 534 days.

(21) Appl. No.: 12/376,779

(22) PCT Filed: Aug. 7, 2007

(86) PCT No.: PCT/EP2007/058180
§ 371 (c)(1),
(2), (4) Date: Feb. 6, 2009

(87) PCT Pub. No.: WO2008/017669
PCT Pub. Date: Feb. 14, 2008

(65) Prior Publication Data
US 2009/0247759 A1    Oct. 1, 2009

Related U.S. Application Data

(60) Provisional application No. 60/836,856, filed on Aug. 9, 2006.

(30) Foreign Application Priority Data

Aug. 9, 2006   (EP) ..................................... 06118690

(51) Int. Cl.
*C07D 215/18* (2006.01)
(52) U.S. Cl. ....................................................... 546/174
(58) Field of Classification Search .................. None
See application file for complete search history.

(56) References Cited

U.S. PATENT DOCUMENTS

| 4,814,477 | A  | * | 3/1989  | Wijnberg et al. ............... 558/86 |
| 2005/0107426 | A1 | * | 5/2005 | Overeem et al. ............... 514/311 |
| 2005/0107612 | A1 |   | 5/2005 | Reguri et al. |
| 2005/0234241 | A1 |   | 10/2005 | Sundaram et al. |

FOREIGN PATENT DOCUMENTS

| CN | 1420113 A | 5/2003 |
| CN | 1428335 A | 7/2003 |
| EP | 0480717 A1 | 4/1992 |
| EP | 0737186 B1 | 8/1998 |
| WO | WO2004108679 A1 | 12/2004 |
| WO | WO2005074935 A1 | 8/2005 |
| WO | WO2005105749 A2 | 11/2005 |
| WO | WO2005105750 A1 | 11/2005 |
| WO | WO2005105751 A1 | 11/2005 |
| WO | WO2006008751 A2 | 1/2006 |
| WO | WO2006043846 A1 | 4/2006 |
| WO | WO2007004237 A2 | 1/2007 |
| WO | WO2007005965 A1 | 1/2007 |
| WO | WO2007012075 A2 | 1/2007 |
| WO | WO2007069261 A1 | 6/2007 |
| WO | WO2007072114 A1 | 6/2007 |
| WO | WO2007096875 A2 | 8/2007 |
| WO | WO2007096889 A2 | 8/2007 |
| WO | WO2007107297 A1 | 9/2007 |
| WO | WO2007116240 A1 | 10/2007 |
| WO | WO2008001213 A1 | 1/2008 |
| WO | WO2008009970 A2 | 1/2008 |
| WO | WO2008015703 A2 | 2/2008 |

OTHER PUBLICATIONS

Notification of Transmittal of the International Search Report and the Written Opinion of the International Searching Authority or the Declaration, Dec. 17, 2007, European Patent Office.

* cited by examiner

*Primary Examiner* — Janet Andres
*Assistant Examiner* — Timothy R Rozof
(74) *Attorney, Agent, or Firm* — Peter B. Scull; Hamilton, DeSanctis & Cha, LLP

(57) ABSTRACT

It comprises a process for the purification of Montelukast, or its salts or its solvates, including any stereoisomer or mixture thereof, which comprises converting Montelukast acid or a solvate thereof, including any stereoisomer or mixtures thereof, into an amine salt selected from the group consisting of tris-(hydroxymethyl)aminomethane, L-(+)-treo-2-amino-1-phenyl-1,3-propanediol, and L-(+)-α-phenylglycinol salt, in the presence of an appropriate solvent. It also comprises novel salts of Montelukast, in particular, tris-(hydroxymethyl)aminomethane, L-(+)-treo-2-amino-1-phenyl-1,3-propanediol, and L-(+)-α-phenylglycinol salts.

18 Claims, 6 Drawing Sheets

PURIFICATION PROCESS OF MONTELUKAST AND ITS AMINE SALTS

CROSS-REFERENCE TO RELATED APPLICATIONS

The present application is the US national stage application of the Patent Cooperation Treaty (PCT) Application Number PCT/EP2007/058180, filed Aug. 7, 2007, entitled "PURIFICATION PROCESS OF MONTELUKAST AND ITS AMINE SALTS"; which designated the United States of America, inter alia; and which claims priority from the European Patent Application, Number 06118690.4, filed Aug. 9, 2006, and from the U.S. Provisional Patent Application No. 60/836,856, filed Aug. 9, 2006, the subject matter of each of which hereby being specifically incorporated herein by reference for all that they disclose and teach.

The present invention relates to a process for the purification of Montelukast. It also relates to novel salts of Montelukast which are useful in said purification process.

BACKGROUND ART

Montelukast, is the International Non-proprietary Name (INN) of 1-[[[(1R)-1-[3-[(1E)-2-(7-chloro-2-quinolinyl)ethenyl]phenyl]-3-[2-(1-hydroxy-1-methylethyl)phenyl]propyl]sulfanyl]methyl]cyclopropaneacetic acid, and CAS No. 158966-92-8. Montelukast sodium salt (CAS No 151767-02-1) is currently used in treatment of asthma, inflammation, angina, cerebral spasm, glomerular nephritis, hepatitis, endotoxemia, uveitis and allograft rejection.

The structure of Montelukast sodium salt corresponds to formula (I):

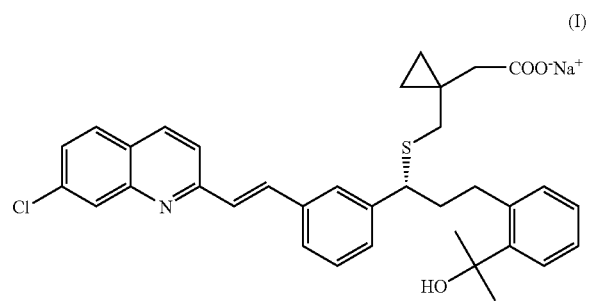

(I)

Different synthetic strategies for the preparation of Montelukast and its salts are known. For instance, EP 480.717 discloses certain substituted quinolone compounds including Montelukast sodium salt, methods for their preparation, and pharmaceutical compositions using these compounds. Several preparation processes of Montelukast sodium salt are reported in this document. Example 161 relates to the preparation of Montelukast sodium salt. According to this Example, preparation of Montelukast sodium salt proceeds through its corresponding methyl ester, whose preparation comprises sodium hydride or cesium carbonate assisted coupling of methyl-1-(mercaptomethyl)-cyclopropaneacetate with the protected mesylate (2-(2-(2-(3(S)-(3-(2-(7-chloro-2-quinolinyl)-ethenyl)phenyl)-3-(methanesulfonyloxy)propyl)phenyl)-2-propoxy)tetrahydropyran, generated in situ. The methyl ester thus obtained is hydrolyzed to the Montelukast acid which is then converted directly to the sodium salt. This process is not particularly suitable for large scale production because it requires tedious chromatographic purification of the methyl ester intermediate and/or the final product, and yields of intermediates and final product are low. Other methods for the preparation of Montelukast and its salts have been described (cf. WO 04/108.679, US 2005/107612, WO 05/105751, WO 05/105749, WO 05/105750, CN 1428335, and CN 1420113).

Generally, Montelukast and its pharmaceutically acceptable salts are obtained by complex synthetic procedures which cause the formation of several by-products due to competing side reactions. These processes need tedious workups to isolate the Montelukast and its intermediates and thus results in excess time cycle, which in turn rendering the process more costly and less eco friendly. It is known that the purification of Montelukast is laborious and complex, being difficult to achieve a Montelukast with a high degree of purity since Montelukast and its precursors are unstable to oxygen and light causing a fast degradation. For the above reasons, Montelukast is generally obtained with a low degree of chemical and optical purity.

Some processes for the purification of Montelukast have been described in the art which are based on the formation of its salts. Thus, EP 737.186 relates to a process for the preparation of Montelukast or its salts, which comprises reacting the dilithium dianion of 1-(mercaptomethyl)-cyclopropaneacetic acid with the corresponding mesylate alcohol ((2-(2-(2-(3(S)-(3-(2-(7-chloro-2-quinolinyl)-ethenyl)phenyl)-3-(methanesulfonyloxy)-propyl)phenyl)-2-propanol), to obtain Montelukast. The crude acid is purified through the formation of its dicyclohexyl amine salt. Depending on the solvent used two crystalline forms of the salts can be obtained, so seeding plays a very critical role during crystallization. Patent application US 2005/234241 also describes a process for the preparation of Montelukast which occurs via the formation of organic Montelukast base salts. In particular, Examples 2 describe the formation of the tert-butylamine salt of Montelukast. Patent application WO 06/008751 also describes a process for the preparation of Montelukast and a process for its purification via the formation of several organic Montelukast base salts.

According to WO 05/074935, Montelukast sodium can be purified by obtaining Montelukast free acid as a solid and converting the Montelukast free acid into Montelukast sodium.

Therefore, from what is known in the art it is derived that the provision of a purification process of Montelukast, and its pharmaceutical acceptable salts which proceeds with high yield and high optical purity, is interesting for the industrial manufacture of these compounds.

SUMMARY OF THE INVENTION

Inventors have found that Montelukast can be obtained with a high optical purity and with high yield through the conversion into an amine salt of Montelukast selected from tris-(hydroxymethyl)aminomethane, L-(+)-treo-2-amino-1-phenyl-1,3-propanediol, and L-(+)-α-phenylglycinol salts. These amine salts have in common that are chiral amines and that the amino moiety is substituted by at least one substituent containing an hydroxyl substituted ethylene group. Compared with other known salts of Montelukast, in particular the dicyclohexylamine or tert-butylamine salt of Montelukast, the salts of the present invention allow to prepare Montelukast with higher optical purity. The purification is surprisingly high in those cases where a Montelukast crude with a low optical purity is used as starting material. Montelukast can be obtained by an easily industrializable process, which is simple and cost-effective. Additionally, Montelukast can be prepared with a high chemical purity.

Thus, according to a first aspect of the present invention, it is provided a process for the purification of Montelukast, or pharmaceutically acceptable salts thereof, or solvates thereof, including stereoisomers or mixtures thereof, which comprises converting Montelukast acid or a solvate thereof, including stereoisomers or mixtures thereof, into an amine salt selected from, tris-(hydroxymethyl)aminomethane, L-(+)-treo-2-amino-1-phenyl-1,3-propanediol, and L-(+)-α-phenylglycinol salts, in the presence of an appropriate solvent.

The invention also refers to a process of purification further comprising a previous purification step which comprises to carry out a specific set of selective extractions of Montelukast or its impurities in a mixture of an organic solvent and water at specific ranges of pH and temperature. Thus, Montelukast can be obtained with a high chemical purity.

Another aspect of the present invention is the use of the amine salts of Montelukast of the present invention to prepare Montelukast acid or its pharmaceutically acceptable salts.

Finally, it is also part of the present invention the provision of novel salts of Montelukast, in particular the following salts of Montelukast: tris-(hydroxymethyl)aminomethane salt, L-(+)-treo-2-amino-1-phenyl-1,3-propanediol salt, and L-(+)-α-phenylglycinol salt including its methanol, ethanol or 2-propanol solvate.

Good results have also been obtained regarding chemical and optical purity through the formation of the cyclohexylamine salt of the Montelukast and, therefore, the purification of Montelukast through its formation as well as the cyclohexylamine salt of Montelukast as product per se forms also part of the present invention.

DETAILED DESCRIPTION OF THE INVENTION

As it is mentioned above, the purification process of the present invention occurs through the formation of an amine salt of Montelukast, which is selected from the following ones: tris-(hydroxymethyl)-aminomethane, L-(+)-treo-2-amino-1-phenyl-1,3-propanediol, and L-(+)-α-phenylglycinol salt. The last one has been found to exist in different solvated forms. Thus, the methanol, ethanol and 2-propanol solvates of the L-(+)-α-phenylglycinol salt of Montelukast form also part of the invention. These salts of Montelukast give the X-Ray diffractograms shown in FIGS. 1-5. X-Ray diffractograms were registered using a PANalytical X'Pert PRO diffractometer at a Cu—Kα1 radiation ($\lambda$=1.5406 Å) and at a power of 45 kV-40 mA.

The best results on the purification of Montelukast are obtained when the amine salts are prepared with L-(+)-treo-2-amino-1-phenyl-1,3-propanediol or L-(+)-α-phenylglycinol. Thus, in a preferred embodiment, the amine salt is L-(+)-treo-2-amino-1-phenyl-1,3-propanediol, and in another preferred embodiment the amine salt is L-(+)-α-phenylglycinol salt. In a more preferred embodiment the salt is the ethanol solvate of L-(+)-α-phenylglycinol salt.

Although the amines used are chiral amines, their use allows to obtain good results without the process going up in price, since these amines are not expensive as chiral products. Particularly cheap is the L-(+)-α-phenylglycinol.

The methanol, ethanol or 2-propanol solvates of the L-(+)-α-phenylglycinol salt of Montelukast can be prepared by the general method described in the Examples for the preparation of the amine salts of Montelukast of the present invention using the corresponding alcohol as solvent of crystallization or by recrystallization in the corresponding alcohol of the L-(+)-α-phenylglycinol salt of Montelukast previously formed in another solvent.

Montelukast acid is used as starting material to prepare the amines mentioned above. It can be provided as a solid or as a solution in an appropriate solvent. Preferably, the amine salt of Montelukast is prepared in a solvent selected from ($C_2$-$C_8$)-ether, ($C_4$-$C_8$)-alkyl ester, ($C_6$-$C_8$)-aromatic hydrocarbon, ($C_6$-$C_8$)-aliphatic hydrocarbon, ($C_2$-$C_5$)-alcohol, and mixtures thereof. More preferably, the solvent is selected from toluene, ethyl acetate, ethanol, 2-propanol, and mixtures thereof.

Generally, the amount of amine varies from 0.5 to 2 equivalents of amine per equivalent of Montelukast. Preferably, the amount of amine is between 0.95 and 1.05 equivalent. The preparation of the amine salt of Montelukast is carried out at a temperature between 0° C. and reflux temperature, preferably between 0° C. and room temperature.

Optionally, the obtained amine salt of Montelukast can be treated with an appropriate solvent between 0° C. and reflux temperature. The isolation of the amine salt of Montelukast can be done by a conventional method such as filtration. Preferably the appropriate solvent is the same as the one used in the previous step of preparation of the amine salt of Montelukast.

The results obtained regarding the optical purification of the amine salts of the present invention are detailed in Table 1 (given below) and in the examples. The enantiomeric excess (e.e.) of the starting Montelukast acid used was 98.8%. Unlike of what is described in the prior art these salts are obtained with meaningful higher purities and also with higher yields.

TABLE 1

| Example | Amine | Solvent | Yield (%) | e.e (%) |
|---|---|---|---|---|
| 12 | Tris-(hydroxymethyl) aminomethane | Toluene | 18 | 99.1 |
| 13 | L-(+)-Treo-2-amino-1-phenyl-1,3-propanediol | AcOEt | 52 | 99.8 |
| 14 | L-(+)-Treo-2-amino-1-phenyl-1,3-propanediol | Toluene | 83 | 99.7 |
| 15 | L-(+)-Treo-2-amino-1-phenyl-1,3-propanediol | Ethanol | 21 | 99.7 |
| 16 | L-(+)-α-phenylglicinol | Toluene | 69 | 99.8 |
| 17 | L-(+)-α-phenylglycinol | AcOEt | 66 | 99.7 |
| Comparative example 7 | t-butylamine | AcOEt | 9 | 99.1 |
| Comparative example 8 | t-butylamine | Acetone | 26 | 99.5 |

As it is mentioned above, the purification is surprisingly high in those cases where a Montelukast crude with a low optical purity is used as starting material. This fact is detailed in a comparative manner in Table 2 below.

TABLE 2

| Example | e.e. (%) crude Montelukast acid | amine | Yield (%) | e.e (%) |
|---|---|---|---|---|
| 20 | 95.2 | L-(+)-Treo-2-amino-1-phenyl-1,3-propanediol | 55 | 99.8 |
| 21 | 95.2 | L-(+)-α-phenylglycinol | 82 | 99.5 |
| Comparative example 19 | 95.2 | diciclohexylamine | 19 | 96.5 |
| Comparative example 29 | 96.8 | t-butylamine | 60 | 97.7 |

Additionally, Montelukast can be prepared with a high chemical purity. This fact is detailed in Table 3 below.

TABLE 3

| Example | Purity by HPLC crude montelukast acid | e.e. (%) crude montelukast acid | amine | Yield (%) | Purity by HPLC | e.e (%) |
|---|---|---|---|---|---|---|
| 22 | 93.8 | 99.4 | L-(+)-α-phenylglycinol | 91 | 98.9 | 99.9 |
| 30 | 89.1 | 99.1 | L-(+)-α-phenylglycinol | 90 | 98.3 | 99.6 |
| Comparative Example 8 | 95.5 | 98.8 | t-butylamine | 26 | 97.3 | 99.5 |
| Comparative Example 29 | 97.6 | 96.8 | t-butylamine | 60 | 98.6 | 97.7 |

The results show that a meaningful higher chemical purity is achieved even where a Montelukast crude with a low chemical purity is used as starting material by the formation of the amine salts of the present invention instead of the salts known in the art As it is mentioned above, cyclohexylamine salt of Montelukast also shows good results regarding its chemical and optical purification, being useful for the purification of Montelukast through its formation. This salt of Montelukast gives the X-Ray diffractogram shown in FIG. 6.

In a preferred embodiment, the purification process of the present invention further comprises a previous purification which comprises carrying out a set of specific selective extractions of Montelukast or its impurities in a mixture of an organic solvent and water at specific ranges of pH and temperature, thereby Montelukast with higher chemical purity is obtained, said set of solvent extractions comprise at least one wash of an aqueous phase containing crude Montelukast in salt form with an organic solvent, at a pH comprised between 12.0 and 13.5 and at a temperature comprised between 10° C. and about 5° C. below the boiling point of the mixture. The aqueous solution containing the Montelukast in salt form may be obtained, for instance, by adding to a mixture of Montelukast acid in an organic solvent, an aqueous solution of a base. In a more preferred embodiment, the set of solvent extractions comprises the following steps: (a) carrying out at least one wash of an aqueous phase containing crude Montelukast in salt form with an organic solvent, at a pH comprised between 12.0 and 13.5 and at a temperature comprised between 10° C. and about 5° C. below the boiling point of the mixture, followed by separating the aqueous phase containing the Montelukast in salt form; (b) optionally, carrying out one or more washes of the aqueous phase of step (a) with an organic solvent at a pH comprised between 8.5 and 10.0 and at a temperature comprised between 10° C. and about 5° C. below the boiling point of the mixture, followed by separating the aqueous phase containing the Montelukast in salt form; (c) carrying out an extraction of the purified Montelukast from the aqueous phase of steps (a) or (b) with an organic solvent at a pH comprised between 4.5 and 8.0 and at a temperature comprised between 10° C. and about 5° C. below the boiling point of the mixture, followed by separating the organic phase containing the Montelukast acid; and (d), optionally isolating the Montelukast from the organic phase of step (c) as acid. The organic phase of step c) or the isolated Montelukast acid of step (d) may be converted into an amine salt from those mentioned above. Thus, Montelukast may be isolated from the organic phase of step (c) in salt form by adding an organic base selected from the group consisting of tris-(hydroxymethyl)aminomethane, L-(+)-treo-2-amino-1-phenyl-1,3-propanediol, and L-(+)-α-phenylglycinol and isolating from the reaction medium the corresponding salt of Montelukast. Likewise, Montelukast may be isolated from the organic phase of step (c) in form of cyclohexylamine salt by adding cyclohexylamine and isolating the salt formed.

Among the impurities that may be effectively removed with the selective extractions of the present invention are the following ones.

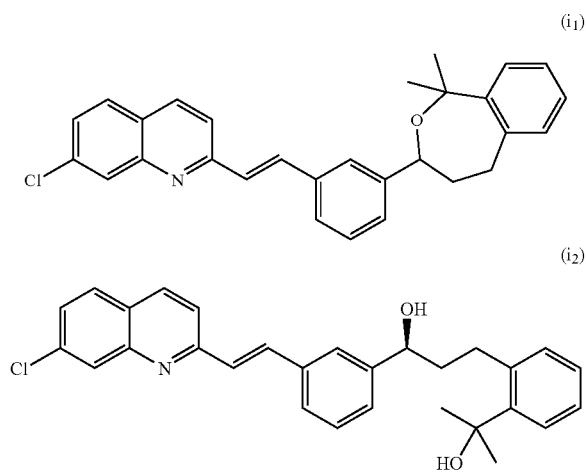

These impurities generally present in Montelukast may be effectively removed with solvent extractions of an aqueous phase containing Montelukast in salt form, at a pH comprised between 12.0 and 13.5.

Other impurities that may be present in Montelukast are the following ones.

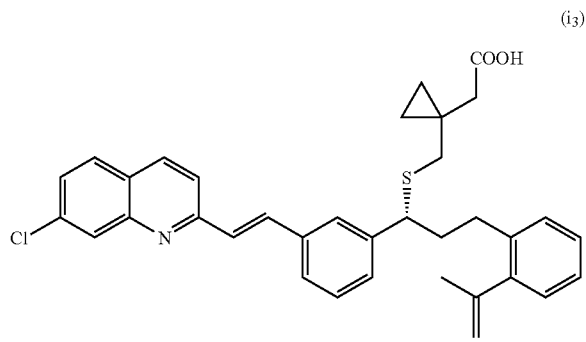

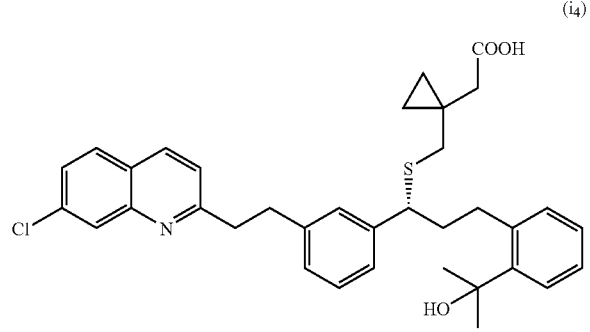

(i4)

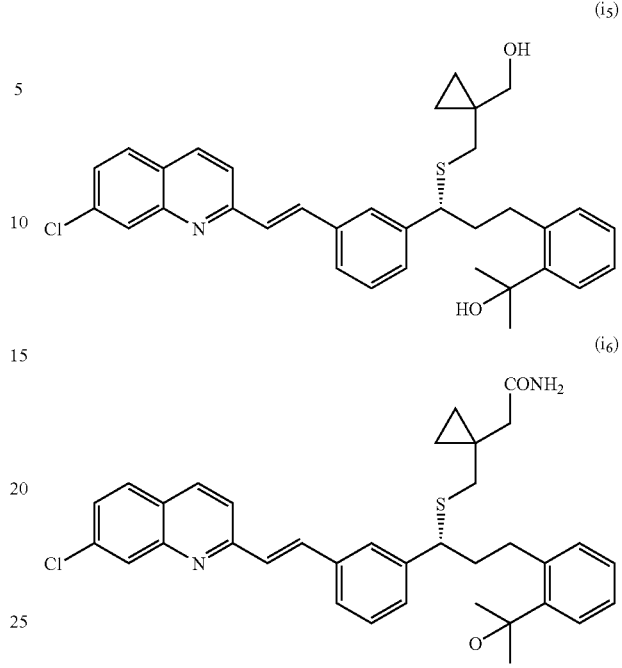

(i5)

(i6)

These impurities, if they are present, may be effectively removed with solvent extractions of an aqueous phase containing Montelukast in salt form at a pH comprised between 8.5 and 10.0.

Preferably, the solvent of the selective extractions is selected from the group consisting of $(C_2-C_8)$-ether, $(C_6-C_8)$-aromatic hydrocarbon, $(C_1-C_3)$-chlorine containing solvents, and mixtures thereof. More preferably, the solvent is selected from toluene, tert-butyl methyl ether, tetrahydrofuran, and mixtures thereof. Preferably, two or three washes at a pH comprised between 12.0 and 13.5 are carried out. Preferably, said washes of step (a) are carried out at a pH comprised between 12.0 and 13.5 and at a temperature comprised between 20 and 60° C. More, preferably, at least two washes are carried out at said pH and temperature. Also preferably, the washes of step (b) are carried out at a pH comprised between 9.0 and 9.5 and at a temperature comprised between 20 and 60° C. The most appropriate temperature conditions vary depending mainly on the solvent used. The temperature can be readily determined by the skilled person in the art with the help of the teaching of the examples given in the description.

This purification process is especially useful to purify Montelukast obtained from the corresponding cyano intermediate of formula (II) by reaction with an inorganic base in a mixture of an $(C_1-C_6)$-alcohol and water.

(II)

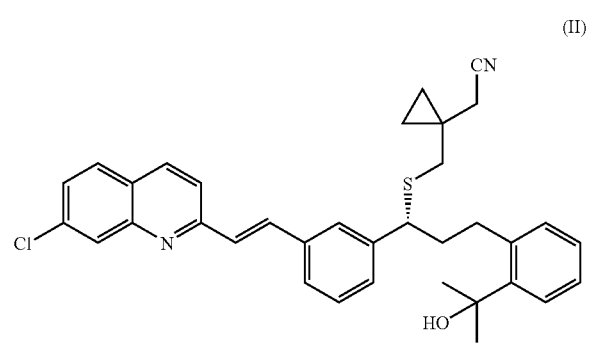

The specific impurities derived of this process may be effectively removed with the solvent extractions of the aqueous phase containing Montelukast in salt form, at a pH comprised between 12.0 and 13.5. Among these impurities there are the cyano compound used as starting material and the following impurities:

In such a case the purification process further comprises a previous step where a compound of formula (II) is reacted with an inorganic base in a mixture of an $(C_1-C_6)$-alcohol and water, to give Montelukast crude of formula (I) in form of salt. In such a case, at the end of the reaction, the alcohol may be separated, for instance, by distillation. Then an organic solvent and water can be added to the crude of the reaction in order to separate an aqueous phase containing the salts from the organic phase containing the Montelukast in salt form. The Montelukast in salt form can be extracted of the organic phase with water. To the resulting aqueous solution containing the Montelukast in salt form is carried out the purification process described above.

The amine salts of Montelukast of the present invention are used to prepare Montelukast. Thus, they can be converted to Montelukast acid by treatment with an organic acid such as formic acid, acetic acid, propanoic acid, or butyric acid, or an inorganic acid such as chlorohydric acid. Preferably, the conversion is carried out in a mixture of an organic solvent and water. More preferably, the organic solvent is toluene or tert-butyl methyl ether. The conversion can be carried out at a temperature comprised between 0° and about 10° C. below the boiling point of the mixture. More preferably, it is carried out at a temperature comprised between 40° C. and about 10° C. below the boiling point of the mixture. The isolation of the product can be done by a conventional method such as filtration. There is no lost of optical purity when Montelukast acid or its pharmaceutically acceptable salts are obtained from the Montelukast amine salts object of this invention.

Montelukast acid can be converted into a pharmaceutically acceptable salt, preferably the sodium salt, by treatment, for instance, with a base such as sodium hydroxide, sodium carbonate, sodium methoxide, or sodium tert-butoxide. Likewise, the amine salt of Montelukast can also conveniently be converted into a pharmaceutically acceptable salt, preferably a sodium salt using, for instance, sodium methoxide or sodium hydroxide.

The best conditions to carry out the process of the present invention vary according to the parameters considered by a person skilled in the art, such as the starting materials, molar ratio, temperature, and similar. Such reaction conditions may be easily determined by a person skilled in the art by routine tests, and with the teaching of the examples included in this document.

Throughout the description and claims the word "comprise" and variations of the word, are not intended to exclude other technical features, additives, components, or steps. The abstract of this application is incorporated herein as reference. Additional objects, advantages and features of the invention will become apparent to those skilled in the art upon examination of the description or may be learned by practice of the invention. The following examples are provided by way of illustration, and they are not intended to be limiting of the present invention.

EXAMPLES

Example 1

Figure 1:
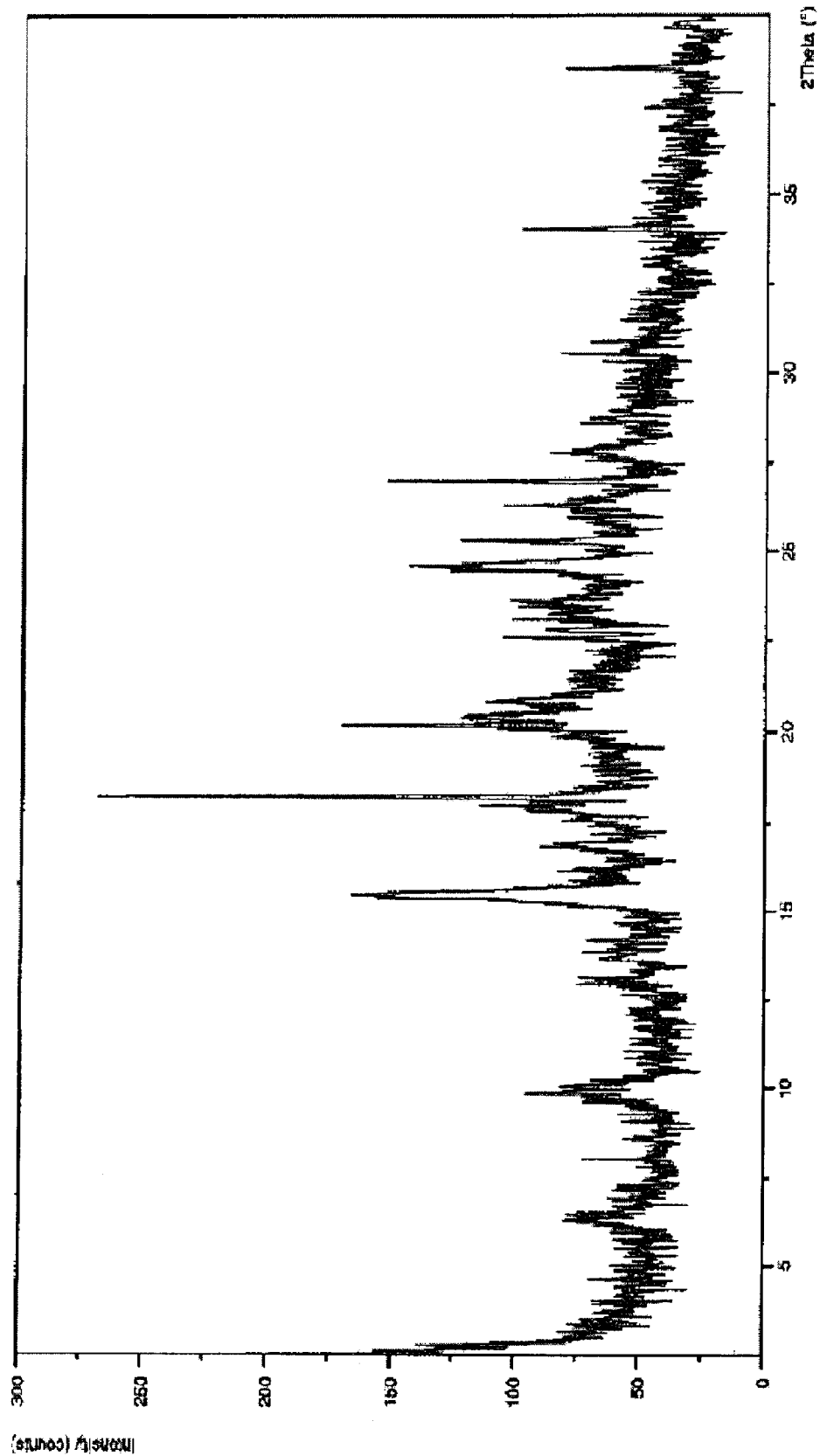
FIG. 1 shows the X-ray powder diffraction pattern of the tris-(hydroxymethyl)aminomethane salt of Montelukast.
Figure 2:
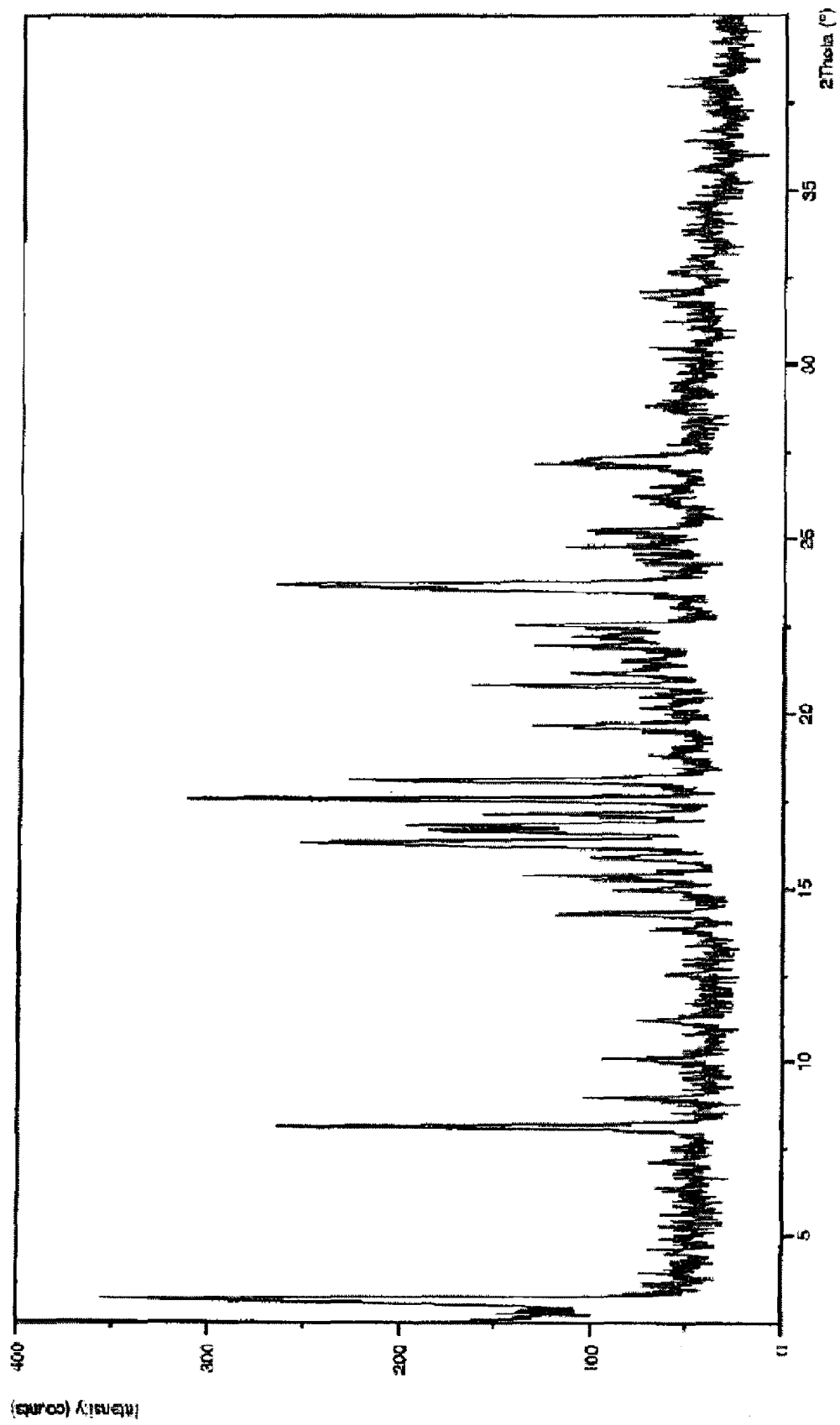
FIG. 2 shows the X-ray powder diffraction pattern of the L-(+)-treo-2-amino-1-phenyl-1,3-propanediol salt of Montelukast

Purification of Montelukast Acid Using Toluene as Solvent for the Extractions 45 ml of an aqueous solution of NaOH 0.5M were added to a 30 ml suspension of Montelukast acid (impurity $i_2$: 0.05 area %; impurity $i_3$: 1.39 area %; impurity $i_5$: 0.20 area %; impurity $i_6$: 0.05 area %) and toluene. A two layer solution was formed where Montelukast appeared dissolved in the aqueous layer as a sodium salt. After 30 minutes of stirring at 40° C., the organic layer was discarded. Another two more washes with 30 ml of toluene were successively carried out adjusting the pH each time between 12.2 and 13.2. The outcome aqueous solution was acidified to pH 9.3 with an aqueous 2M solution of acetic acid and washed twice with 30 ml of toluene. Both extractions were carried out at 60° C. Finally, another 30 ml of toluene were added to the aqueous solution and the mixture was acidified to pH 6.0 with an aqueous 2M solution of acetic acid at room temperature. The final organic layer was separated and kept as a solution of purified Montelukast acid (Purity by HPLC: 96.8 area %; impurity $i_2$: 0.02 area %; impurity $i_3$: 1.23 area %; impurity $i_5$: not detected; impurity $i_6$: not detected %). Yield: 83%

Example 2

Purification of Montelukast Acid Using Tert-Butyl Methyl Ether as Solvent for the Extractions 45 ml of an aqueous solution of NaOH 0.5M were added to a 30 ml suspension of Montelukast acid (Purity by HPLC: 97.4 area %; impurity $i_2$: 0.05 area %; impurity $i_3$: 1.39 area %; impurity $i_5$: 0.20 area %; impurity $i_6$: 0.05 area %) and tert-butyl methyl ether. A two layer solution was formed where Montelukast appeared dissolved in the aqueous layer as a sodium salt. After 30 minutes of stirring at room temperature, the organic layer was discarded. Another two more washes with 30 ml of tert-butyl methyl ether were successively carried out adjusting the pH each time between 12.5 and 13.5 at room temperature. The outcome aqueous solution was acidified to pH 9.2 with an aqueous 2M solution of acetic acid and washed twice with 30 ml of tert-butyl methyl ether at room temperature. Finally, another 30 ml of toluene were added to the aqueous solution and the mixture was acidified to pH 7.7 with an aqueous 2M solution of acetic acid. The final organic layer was separated and kept as a solution of purified Montelukast acid (chemical purity by HPLC: 97.7 area %; impurity $i_2$: not detected; impurity $i_3$: 1.11 area %; impurity $i_5$: not detected; impurity $i_6$: not detected). Yield: 67%.

Example 3

Preparation of Montelukast Acid 143.6 g of sodium hydroxide were added to a solution of 102 g of (R,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetonitrile in 407 ml of ethanol 96% (v/v). The mixture was stirred at reflux temperature for 30 hours. After this period of time, the solvent was distilled off under vacuum (Purity by HPLC: 61.5 area %; impurity $i_2$: 1.84 area %; impurity $i_5$: 3.70 area %; impurity $i_6$: 1.42 area %). The mixture was partitioned with 1000 ml of toluene and 1500 ml of water at room temperature. The aqueous phase with the inorganic salts dissolved, was discarded. The organic phase was mixed with 1500 ml of water and the mixture was heated to 60° C. and stirred for 15 minutes. At this point the product was dissolved in the aqueous layer. The pH of the aqueous layer was 12.5. Some impurities from the process were dissolved in the organic layer. Therefore, the organic layer was discarded. The toluene wash at 60° C. was repeated. The outcome aqueous layer was cooled down to room temperature and 1000 ml of toluene were added. Then, the pH of the mixture was adjusted to 5.6 with a 2M solution of acetic acid. The mixture was stirred for 30 minutes and the aqueous layer was discarded. Finally, the organic layer was washed with 1000 ml of water and kept as a solution of purified Montelukast acid (Purity by HPLC: 84.4 area %; impurity $i_2$: 0.81 area %; impurity $i_5$: 0.70 area %; impurity $i_6$: 0.007 area %). Yield corrected by HPLC of the title compound from the outcome solution: 86%.

Example 4

Crystallization of Montelukast Acid

The toluene solution obtained in the previous example was stirred at room temperature for 12 hours. After this period of time, a yellow suspension was formed. The outcome solid was filtered off, washed with toluene and dried under vacuum at 30° C. for 24 hours. 53 g of Montelukast acid were recovered (Purity by HPLC: 96 area %). Yield corrected by HPLC: 90%.

Examples 5-8 (Comparative Examples)

In comparative example 5 the dicyclohexylamine salt of Montelukast has been prepared in the conditions described in Example 13 of EP737186. Comparative example 6 corresponds to the preparation of the dicyclohexylamine salt of Montelukast in the conditions described in Example 2 of WO 04/108679. Comparatives examples 7 and 8 are based on the process described in Example 2 of US2005/234241. The enantiomeric excess (e.e.) of the starting Montelukast acid used in comparative examples 5 to 8 was 98.8% and the chemical purity by HPLC: 95.5%. The enantiomeric excess (e.e.) was measured by chiral HPLC. The results are summarized in Table 4.

TABLE 4

| Comparative Examples | Amine | Solvent | Yield (%) | e.e. (%) |
|---|---|---|---|---|
| 5 | Dicyclohexylamine (1.2 equivalents) | Toluene/Heptane | 90 | 99.1 |
| 6 | Dicyclohexylamine (1.2 equivalents) | AcOEt/Toluene | 61 | 99.5 |
| 7 | t-Butylamine | Ethyl acetate | 9 | 99.1 |
| 8 | t-Butylamine | Acetone | 26 | 99.5 |

The chemical purity obtained for the t-butylamine salt of Comparative Example 8 is 97.3%.

General Process for the Preparation of an Amine of Montelukast 1.0 equivalent of the amine was added in one portion to a suspension of 0.5 g of Montelukast acid (e.e.: 98.8%) in 2 ml of solvent. If required, the suspension was heated until dissolution was achieved. After 18 hours of stirring at room temperature, the outcome suspension was filtered. The obtained solid was dried under vacuum at 30° C. for 24 hours. The general process has been repeated using the corresponding amines and solvents indicated in Table 5. Example 9 was has been carried out using 5.0 g of Montelukast acid. Example 16 has been carried out using 2.4 g of Montelukast acid. The enantiomeric excess (e.e.) of the starting Montelukast acid used in examples 9-18 was 98.8%.

The enantiomeric excess (e.e.) was measured by chiral HPLC. DSC measurements were carried out in a perforated pan at a scan rate of 10° C./minute from 25.0° C. to 250.0° C. under a nitrogen purge with a DSC Mettler Toledo DSC822e.

TABLE 5

| Example | Amine | Solvent | Yield (%) | e.e. (%) | DSC (° C.) |
|---|---|---|---|---|---|
| 9 | Cyclohexylamine | Toluene | 68 | 99.3 | 134.1 |
| 10 | Cyclohexylamine | Ethyl acetate | 53 | 99.3 | 134.1 |
| 11 | Cyclohexylamine | 2-Propanol | 55 | 99.3 | 134.1 |
| 12 | Tris-(hydroxymethyl) aminomethane | Toluene | 18 | 99.1 | 134.4 |
| 13 | L-(+)-Treo-2-amino-1-phenyl-1,3-propanediol | Ethyl acetate | 52 | 99.8 | 120.8 |
| 14 | L-(+)-Treo-2-amino-1-phenyl-1,3-propanediol | Toluene | 83 | 99.7 | 120.8 |
| 15 | L-(+)-Treo-2-amino-1-phenyl-1,3-propanediol | Etanol | 21 | 99.7 | 120.8 |
| 16 | L-(+)-α-Phenylglycinol | Toluene | 69 | 99.8 | 110.7 |
| 17 | L-(+)-α-Phenylglycinol | Ethyl acetate | 66 | 99.7 | 110.7 |
| 18 | L-(+)-α-Phenylglycinol | 2-Propanol | 19 | 99.5 | 79.9 |

Figure 3:
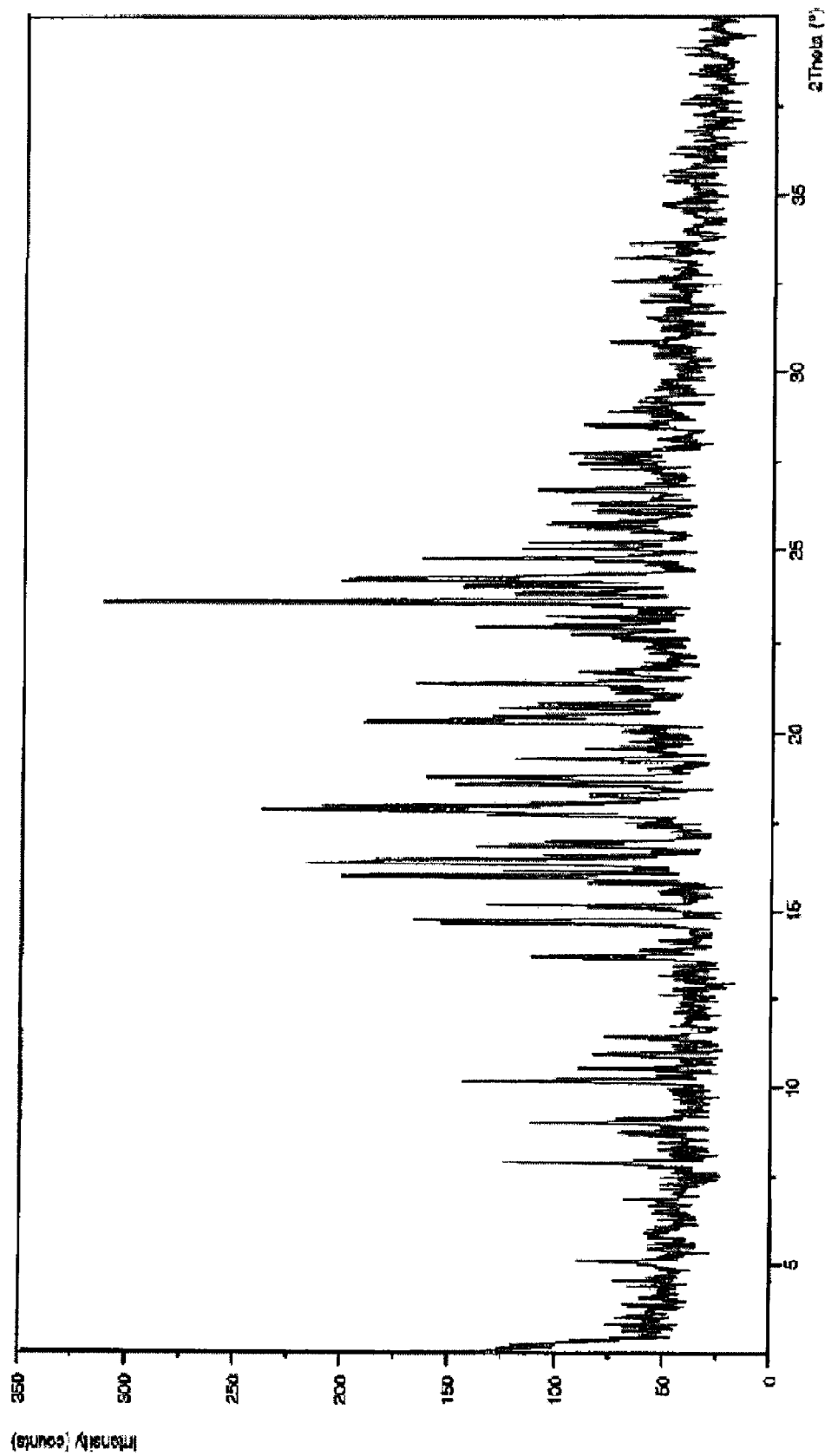
FIG. 3 shows the X-ray powder diffraction pattern of L-(+)-α-phenylglycinol salt of Montelukast

The L-(+)-α-phenylglycinol salt of Montelukast obtained in Example 17 gives the X-Ray diffractogram shown in FIG. 3.

Example 19 (Comparative Example)

Preparation of the Dicyclohexylamine Salt of Montelukast from a Montelukast Acid with a e.e. of 95.2%

0.5 g of Montelukast acid (e.e.: 95.2%) were suspended in 5 ml of toluene and 0.11 ml of dicyclohexylamine were added in one portion to obtain a clear pale brown solution. After 8 hours of stirring, 1 ml of heptane was added and the outcome suspension was filtered under vacuum. The obtained solid was dried under vacuum at 30° C. for 24 hours to yield 0.12 g of the title compound (Yield: 19%, e.e.: 96.5%).

Example 20

Preparation of the L-(+)-treo-2-amino-1-phenyl-1,3-propanediol salt of Montelukast from a Montelukast acid with a e.e. of 95.2%

0.5 g of Montelukast acid (e.e.: 95.2%) were suspended in 5 ml of 2-propanol and 0.14 g of L-(+)-treo-2-amino-1-phenyl-1,3-propanediol were added in one portion. The outcome suspension was heated to obtain a clear pale brown solution. Then, the mixture was cooled down to room temperature and after 4 hours of stirring, the outcome suspension was filtered under vacuum. The obtained solid (e.e. of an aliquot dried under vacuum at 30° C. for 24 hours: 98.6%) was heated in 5 ml of 2-propanol for 15 minutes, cooled down to room temperature for 2 hours and filtered again. The outcome solid was dried under vacuum at 30° C. for 24 hours to yield 0.35 g of the title compound (Yield: 55%, e.e. 99.8%).

Example 21

Preparation of the L-(+)-α-phenylglycinol salt of Montelukast from a Montelukast acid with a e.e. of 95.2%

0.5 g of Montelukast acid (e.e.: 95.2%) were suspended in 5 ml of ethyl acetate and 0.11 g of L-(+)-α-phenylglycinol were added in one portion. The outcome suspension was heated to obtain a clear pale brown solution. Then, the mixture was cooled down to room temperature and after 4 hours of stirring, the outcome suspension was filtered under vacuum. The obtained solid (e.e. of an aliquot dried under vacuum at 30° C. for 24 hours: 98.2%) was heated in 5 ml of ethyl acetate for 15 minutes, cooled down to room temperature for 2 hours and filtered. The outcome solid was dried under vacuum at 30° C. for 24 hours to yield 0.42 g of the title compound (Yield: 82%, e.e.: 99.5%).

Example 22

Preparation of the L-(+)-α-phenylglycinol salt of Montelukast from a Montelukast free acid 189.4 g of Montelukast acid (Purity by HPLC: 93.8 area %, e.e.: 99.4%) were suspended in 1.9 L of toluene and 44.3 g of L-(+)-α-phenylglycinol were added in one portion. The outcome suspension was heated to obtain a clear pale brown solution. Then, the mixture was cooled down to room temperature and after 2 hours of stirring, the outcome suspension was filtered under vacuum. 500 ml of toluene were used to wash the cake. The obtained solid (HPLC purity: 98.4 area %, e.e.: 99.7%) was suspended in 2.9 L of toluene, heated at 80°

C. for 40 minutes, cooled down to room temperature and filtered. Purity by HPLC: 98.9 area %, e.e.: 99.9%. Yield: 91%.

General Process for the Preparation of Montelukast Acid from an Amine Salt of Montelukast The amine salt of Montelukast acid was suspended in 10 volumes of toluene and 10 volumes of water. Then, a solution of 2M acetic acid was added until the pH is decreased below 6. Then, the mixture was heated between 30 and 95° C. and stirred for 30 minutes, cooled and the aqueous layer was discarded. The organic layer was washed with 5 volumes of water and kept as a solution of Montelukast acid.

Example 23

Preparation of Montelukast free acid from L-(+)-α-phenylglycinol salt of Montelukast 169.5 g of the L-(+)-α-phenylglycinol salt of Montelukast (e.e.: 99.9%) were suspended in 1695 ml of toluene. 1695 ml of water were added to the suspension, followed of 170 ml of an aqueous solution of acetic acid 2M. The mixture was heated to 35° C., stirred for 30 minutes and the aqueous layer was discarded. The organic layer was washed twice with 850 ml of water maintaining the temperature at 35° C. The outcome organic solution of Montelukast acid was analysed by chiral HPLC (e.e.: 99.9%). Yield: 97%.

Example 24

Preparation of Montelukast Sodium 2.6 g of Montelukast acid were dissolved in 26 ml of toluene and 8.9 ml of 0.5M NaOH solution in methanol were added slowly at room temperature. The mixture was stirred for 1 hour and the solvent was removed under vacuum to obtain a residue. Then, heptane (24 ml) was added over 30 minutes to a well stirred solution of the residue in 4 ml of ethyl acetate at room temperature. Two hours after the addition, an off white solid was filtered off under a nitrogen atmosphere and washed with 5 ml of heptane. The wet product was dried under vacuum at 70-80° C. for 2 days to yield 2.7 g of Montelukast sodium. Yield: 100%.

Example 25

Preparation of Montelukast Sodium 1.15 L of toluene were added to 115.2 g of Montelukast acid (e.e.: 99.9%). The mixture was cooled between 2 and 10° C. and 313.3 ml of 0.5M NaOH solution in methanol were added over 15 minutes. Then, the mixture was warmed to room temperature and stirred for 30 minutes. After this period of time, 1.5 L of the solvent were distilled off under reduced pressure at 30° C. Then, 2.4 L of toluene were charged to the crude and the distillation was resumed to obtain a final volume of 300 ml. The solution of crude obtained was added over 1 hour to 1 L of heptane under stirring at room temperature. 18 hours after the addition, an off white solid was filtered off under a nitrogen atmosphere and washed with 500 ml of heptane. The wet product was dried under vacuum at 75° C. for 3 days to yield 120 g of Montelukast sodium. Yield: 100%. e.e.: 99.9%.

Example 26

Preparation of the methanol solvate of L-(+)-α-phenylglycinol salt of Montelukast from L-(+)-α-phenylglycinol salt of Montelukast 4.0 g of L-(+)-α-phenylglycinol salt of Montelukast (HPLC: 98.2%) were suspended in 24 ml of methanol and stirred at room temperature until a solution was obtained. The solution was kept at room temperature and quickly a white solid precipitated. Then, the slurry was cooled to 0° C. and the solid was filtered off and dried under vacuum. 3.2 g of the title compound were obtained. Yield: 79%. HPLC: 99.3%. DSC (peak): 91.9° C., 104.0° C. H-RMN (6d-DMSO): 0.6% (mol/mol) of MeOH.

Example 27

Figure 4:
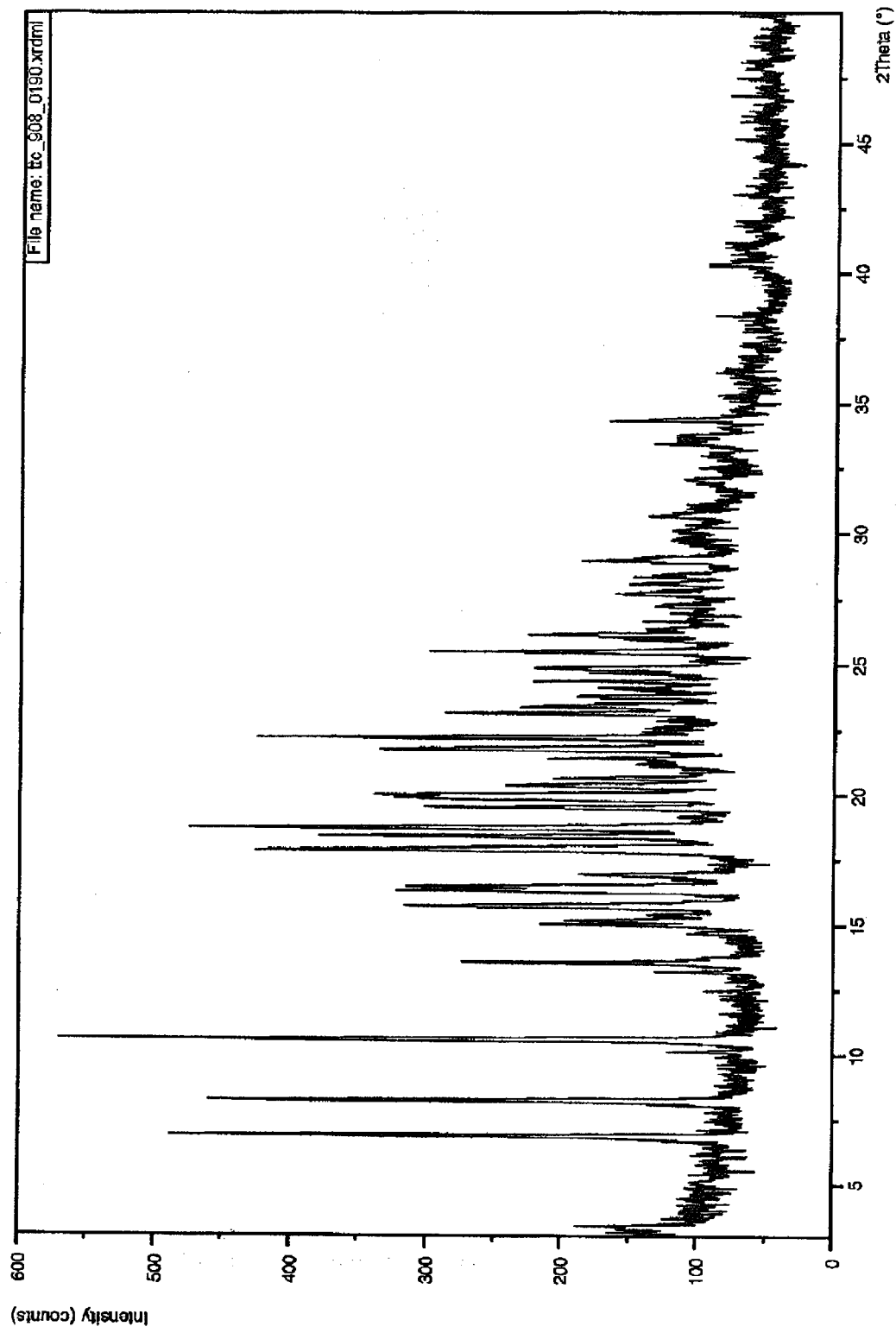
FIG. 4 shows the X-ray powder diffraction pattern of ethanol solvate of L-(+)-α-phenylglycinol salt of Montelukast

Preparation of the ethanol solvate of L-(+)-α-phenylglycinol salt of Montelukast from L-(+)-α-phenylglycinol salt of Montelukast 4.0 g of L-(+)-α-phenylglycinol salt of Montelukast (HPLC: 98.2%) were suspended in 40 ml of ethanol. The suspension was heated to 60° C. until a solution was obtained. The solution was cooled down to 20° C. and kept under stirring at room temperature until an abundant solid precipitated. The slurry was cooled to 0° C. and the solid was filtered off and dried under vacuum. 3.35 g of the title compound were obtained. Yield: 81%. HPLC: 99.2%. DSC (peak): 89.2° C., 95.1° C. H-RMN (6d-DMSO): 0.6% (mol/mol) of EtOH. X-Ray diffractogram shown in FIG. 4

Example 28

Figure 5:
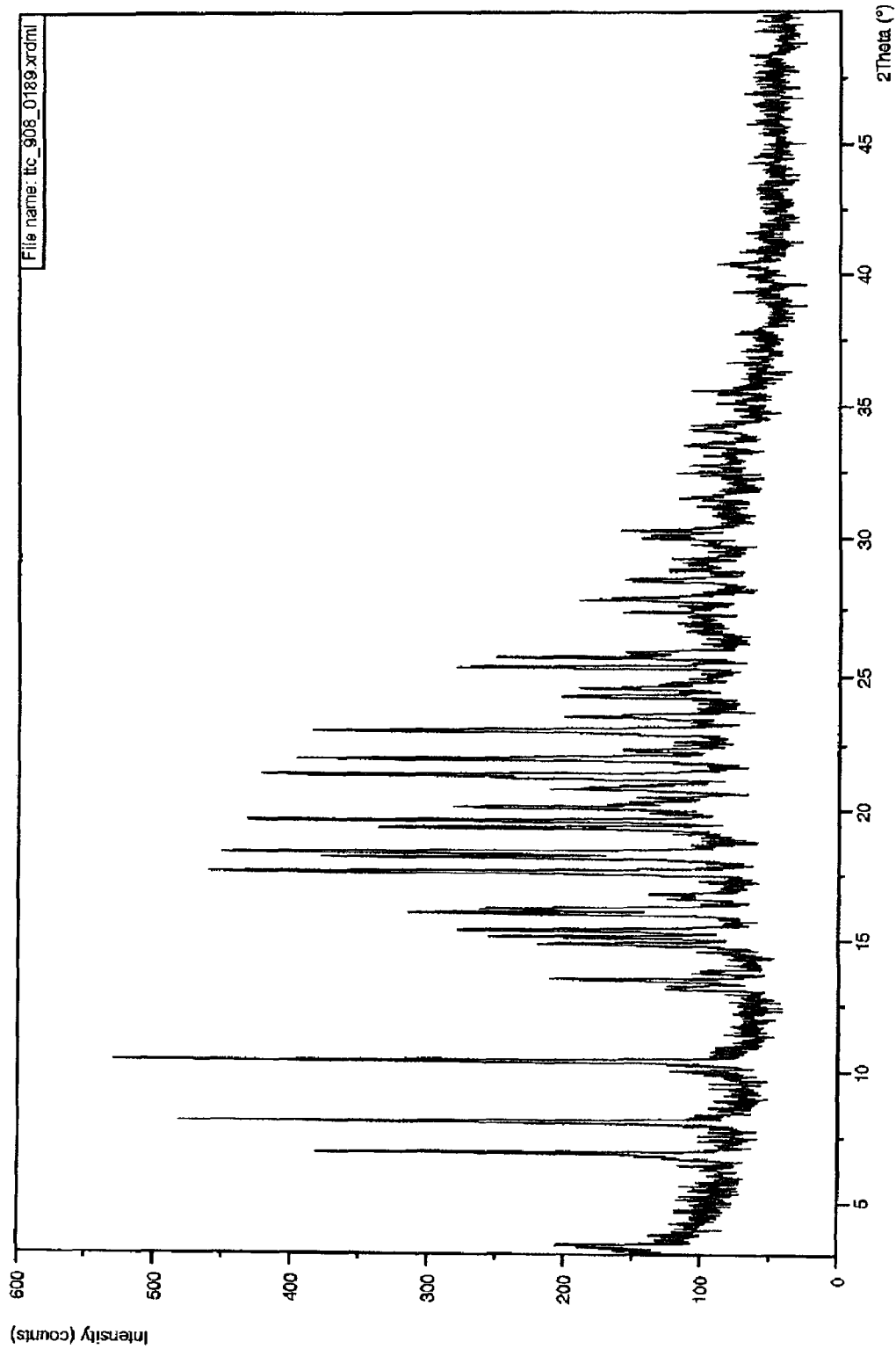
FIG. 5 shows the X-ray powder diffraction pattern of 2-propanol solvate of L-(+)-α-phenylglycinol salt of Montelukast
Figure 6:
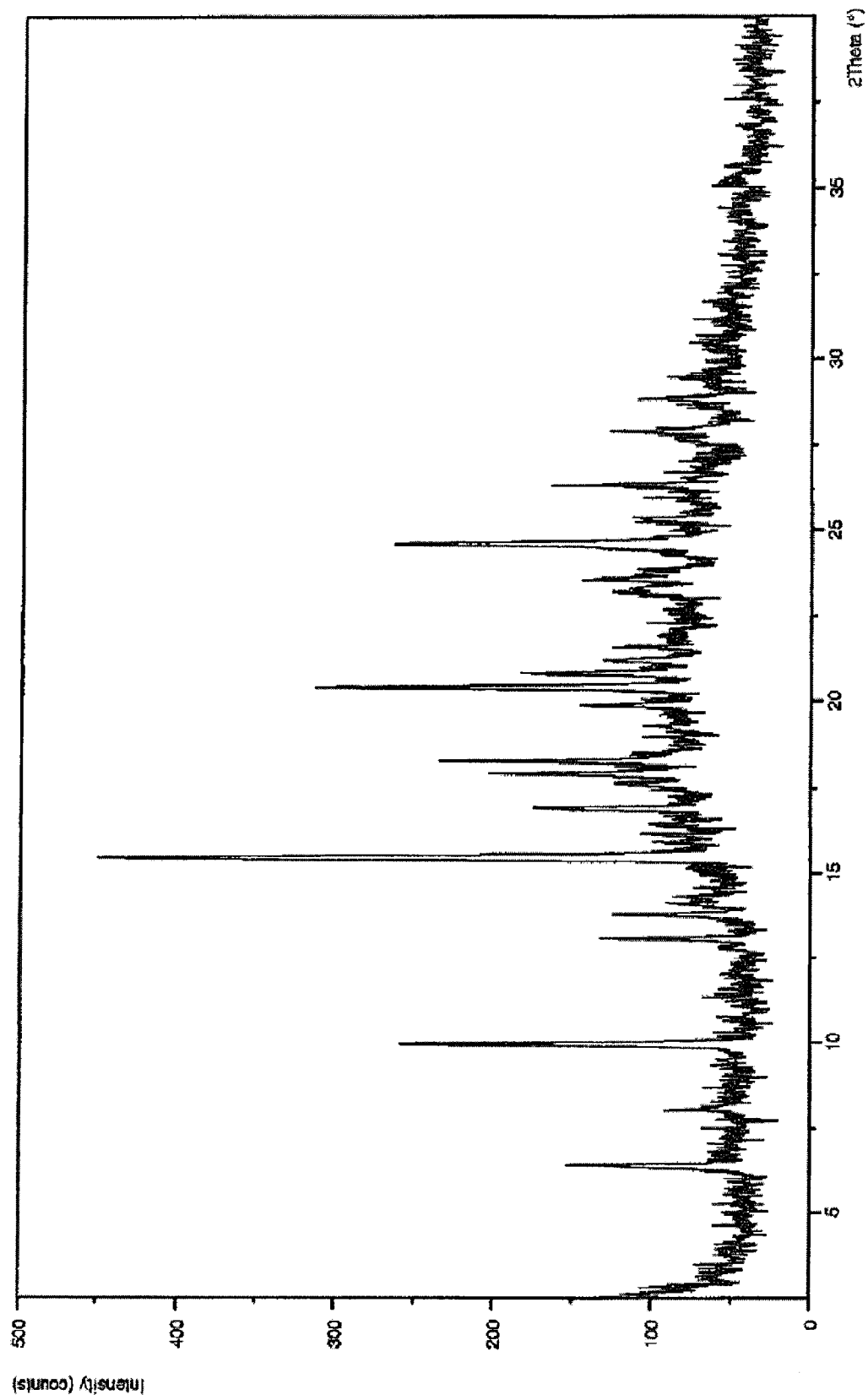
FIG. 6 shows the X-ray powder diffraction pattern of the cyclohexylamine salt of Montelukast

Preparation of the 2-propanol solvate of L-(+)-α-phenylglycinol salt of Montelukast from L-(+)-α-phenylglycinol salt of Montelukast 4.0 g of L-(+)-α-phenylglycinol salt of Montelukast (HPLC: 98.8%) were suspended in 40 ml of 2-propanol. The suspension was heated to 60° C. until a solution was obtained. The solution was cooled down to 20° C. and kept under stirring at room temperature until an abundant solid precipitated. The slurry was cooled to 0° C. and the solid was filtered off and dried under vacuum. 3.64 g of the title compound were obtained. Yield: 86%. HPLC: 99.3%. DSC (peak): 79.9° C. H-RMN (6d-DMSO): 0.6% (mol/mol) of 2-propanol. X-Ray diffractogram shown in FIG. 5.

Example 29

Preparation of the T-Butylamine Salt of Montelukast 1.0 g of Montelukast free acid (purity by HPLC: 97.6%; e.e: 96.8%) were suspended in 10 ml of acetone. 0.25 g of t-butylamine were added in one portion. After 4 hours of stirring at room temperature the mixture was filtered under vacuum. The cake was washed three times with 2 ml of acetone. The outcome solid was dried under vacuum at 25° C. for 24 hours to yield 0.68 g of the title compound (Yield: 60%; purity by HPLC: 98.6%; e.e.: 97.7%).

Example 30

Preparation of the L-(+)-α-phenylglycinol salt of Montelukast

A solution obtained as in the example 3, equivalent to 10 g of Montelukast acid (purity by HPLC: 89.1%; e.e.: 99.1%)

was mixed with 2.4 g of L-(+)-α-phenylglycinol. The outcome suspension was heated to 70° C. and after 10 minutes the mixture was cooled down to room temperature, stirred for 1 hour and filtered under vacuum. The cake was washed twice with 10 ml of toluene and dried under vacuum at 25° C. 10.7 g of the title compound were obtained. Yield: 90%. Purity by HPLC: 98.3 area %. e.e.: 99.6%.

The invention claimed is:

1. A process for the purification of Montelukast, or a pharmaceutically acceptable salt thereof, or a solvate thereof, including any stereoisomer or mixture thereof which comprises converting Montelukast acid or a solvate thereof, including any stereoisomer or mixture thereof, into an amine salt of L-(+)-α-phenylglycinol salts, in the presence of an appropriate solvent.

2. The purification process according to claim 1, wherein the L-(+)-α-phenylglycinol salt of Montelukast is a solvate selected from the group consisting of methanol, ethanol and 2-propanol solvate.

3. The purification process according to claim 1, wherein the solvent is selected from the group consisting of ($C_2$-$C_8$)-ether, ($C_4$-$C_8$)-alkyl ester, ($C_6$-$C_8$)-aromatic hydrocarbon; ($C_6$-$C_8$)-non aromatic hydrocarbon, ($C_2$-$C_5$)-alcohol, and mixtures thereof.

4. The purification process according to claim 3, wherein the solvent is selected from toluene, ethyl acetate, ethanol, 2-propanol, and mixtures thereof.

5. The purification process according to claim 1, further comprising a previous purification process which comprises carrying out a specific set of selective solvent extractions of Montelukast or its impurities, said set of solvent extractions comprising at least one wash of an aqueous phase containing crude Montelukast in salt form with an organic solvent, at a pH between 12.0 and 13.5 and at a temperature between about 10° C. and about 5° C. below the boiling point of the mixture.

6. The purification process according to claim 5, wherein the set of solvent extractions comprises the following steps:
    (a) carrying out at least one wash of an aqueous phase containing crude Montelukast in salt form with an organic solvent, at a pH between 12.0 and 13.5 and at a temperature between about 10° C. and about 5° C. below the boiling point of the mixture, and separating the aqueous phase containing the Montelukast in salt form;
    (b) optionally, carrying out one or more washes of the aqueous phase of step (a) with an organic solvent at a pH between 8.5 and 10.0 and at a temperature between about 10° C. and about 5° C. below the boiling point of the mixture, and separating the aqueous phase containing the Montelukast in salt form;
    (c) carrying out an extraction of the purified Montelukast from the aqueous phase of steps (a) or (b) with an organic solvent at a pH between 4.5 and 8.0 and at a temperature between about 10° C. and about 5° C. below the boiling point of the mixture, and separating the organic phase containing the Montelukast acid; and
    (d) optionally, isolating the Montelukast from the organic phase of step (c) as acid.

7. The purification process according to claim 6, wherein the organic solvent is selected from the group consisting of ($C_2$-$C_8$)-ether, ($C_6$-$C_8$)-aromatic hydrocarbon; ($C_1$-$C_3$)-chlorine containing solvents, and mixtures thereof.

8. The purification process according to claim 7, wherein the solvent is selected from toluene, tert-butyl methyl ether, tetrahydrofuran, and mixtures thereof.

9. The purification process according to claim 5, wherein at least two washes are carried out at a pH between 12.0-13.5 and at a temperature between 20° C. and 60° C.

10. The purification process according to claim 6 wherein the extractions of step (b) are carried out at a pH equal to 9.0-9.5, and at a temperature between 20° C. and 60° C.

11. The purification process according to claim 1, which comprises:
    (a) treating an amine salt of Montelukast as defined in claim 1 with an acid, to obtain Montelukast acid; and optionally,
    (b) treating the product thus obtained with a source of an ion and isolating the corresponding pharmaceutically acceptable salt.

12. The process according to claim 11, wherein the ion is sodium and the pharmaceutically acceptable salt is the sodium salt.

13. A compound which is L-(+)-treo-2-amino-1-phenyl-1,3-propanediol salt of Montelukast.

14. A compound which is L-(+)-α-phenylglycinol salt of Montelukast.

15. A solvate of the L-(+)-α-phenylglycinol salt of Montelukast selected from the group consisting of methanol, ethanol and 2-propanol solvate.

16. The purification process according to claim 4, which comprises:
    (a) treating an amine salt of Montelukast of L-(+)-α-phenylglycinol, with an acid, to obtain Montelukast acid; and optionally,
    (b) treating the product thus obtained with a source of an ion and isolating the corresponding pharmaceutically acceptable salt.

17. A process for the purification of Montelukast, or a pharmaceutically acceptable salt thereof, or a solvate thereof, including any stereoisomer or mixture thereof which comprises converting Montelukast acid or a solvate thereof, including any stereoisomer or mixture thereof, into an amine salt of L-(+)-treo-2-amino-1-phenyl-1,3-propanediol, in the presence of an appropriate solvent.

18. The purification process according to claim 17, which comprises:
    (a) treating an amine salt of Montelukast of L-(+)-treo-2-amino-1-phenyl-1,3-propanediol, with an acid, to obtain Montelukast acid; and optionally,
    (b) treating the product thus obtained with a source of an ion and isolating the corresponding pharmaceutically acceptable salt.

* * * * *